United States Patent [19]

Jackson, Jr. et al.

[11] Patent Number: 4,745,211

[45] Date of Patent: May 17, 1988

[54] PROCESS FOR THE PREPARATION OF PURIFIED BIS(2-HYDROXYETHYL) ESTER OF 2,6-NAPHTHALENEDICARBOXYLIC ACID

[75] Inventors: Winston J. Jackson, Jr.; Thomas H. Wicker, Jr., both of Kingsport, Tenn.

[73] Assignee: Eastman Kodak Company, Rochester, N.Y.

[21] Appl. No.: 96,436

[22] Filed: Sep. 15, 1987

[51] Int. Cl.[4] .............................................. C07C 67/00
[52] U.S. Cl. ..................................... 560/80; 502/167; 502/171; 502/227; 502/350; 560/79; 560/91; 560/93; 560/94; 560/99
[58] Field of Search ....................... 560/79, 80, 91, 93, 560/94, 99; 502/167, 171, 227, 350

[56] References Cited

U.S. PATENT DOCUMENTS

| | | | |
|---|---|---|---|
| 3,666,791 | 5/1972 | Chikawa et al. | 560/79 |
| 3,769,323 | 10/1973 | Ichikawa et al. | 560/79 |
| 4,304,925 | 12/1981 | Watanabe et al. | 560/78 |
| 4,506,091 | 3/1985 | Deardoff | 560/99 |

*Primary Examiner*—Werren B. Lone
*Assistant Examiner*—Vera C. Clarke
*Attorney, Agent, or Firm*—Charles R. Martin; William P. Heath, Jr.

[57] ABSTRACT

A process for preparation of a purified bis(2-hydroxyethyl) ester of 2,6-naphthalenedicarboxylic acid wherein 2,6-naphthalenedicarboxylic acid is reacted with a catalyst comprised of a tertiary amine and a titanium-containing compound in order to produce the ester.

8 Claims, No Drawings

PROCESS FOR THE PREPARATION OF PURIFIED BIS(2-HYDROXYETHYL) ESTER OF 2,6-NAPHTHALENEDICARBOXYLIC ACID

This invention relates to a process for the preparation of purified bis(2-hydroxyethyl) ester of 2,6-naphthalenedicarboxylic acid by reacting impure 2,6-naphthalenedicarboxylic acid with at least 2 moles of ethylene glycol to form the corresponding ester using a catalyst comprising a tertiary amine and a titanium-containing compound. The corresponding ester is then crystallized and recovered.

The preparation of the bis(2-hydroxyethyl) ester of 2,6-naphthalenedicarboxylic acid is well known in the art. For example, synthesis of the ester from the acid and ethylene oxide is described in U.S. Pat. No. 3,641,112. The ester can also be prepared by glycolysis of the polymer in the presence of ethylene glycol as disclosed in JA-75 11,381.

Regardless of the method used for preparation of the ester it contains various impurities, depending upon the preparative process, of the 2,6-naphthalenedicarboxylic acid. When the impure ester is used to prepare polymers, the impurities can cause the polymer to discolor, prevent molecular weight build up and other problems.

The process of our invention can broadly be thought of as comprising the following three steps:
1. preparing the bis(2-hydroxyethyl) ester of 2,6-naphthalenedicarboxylic acid by reacting impure 2,6-naphthalenedicarboxylic acid with at least two moles of ethylene glycol per mole of 2,6-naphthalenedicarboxylic acid in the presence of a catalytic amount of a tertiary amine and a titanium-containing compound,
2. crystallizing the ester, and
3. recovering the purified, crystalized ester.

In the first step of this invention it is important that at least 2 moles of ethylene glycol be used per mole of 2,6-naphthalenedicarboxylic acid. If less than 2 moles are used, incomplete or "half" esters will be formed. Typically, an excess of 2 moles of ethylene glycol is used so that the excess ethylene glycol functions as a solvent and no other solvent is needed. If precisely 2 moles of ethylene glycol are used, a solvent of the type well known in the art is used.

An important feature of this invention is that the preparation of the ester can be conducted at atmospheric pressure and therefore the equipment required is far less costly than if high pressures are used. If desired, the ester forming step can be conducted at elevated pressures.

The ester forming step can be conducted at any temperature sufficient to form the ester; however, temperatures of less than 220° C. are preferred. More preferably a temperature in the range of 180° to 220° C. can be used.

The time required for the reaction between ethylene glycol and 2,6naphthalenedicarboxylic acid can vary depending on the reaction temperature and other variables. Generally speaking the acid is completely esterified during a period of 2–4 hours at a temperature of about 200° C. The time will be shorter when higher temperatures are used.

In accordance with this invention the catalyst used to prepare the ester is comprised of the combination of a tertiary amine and a titanium-containing compound.

The titanium-containing compound used in this invention can be any titanium-containing compound that will result in a significantly enhanced rate of esterification. Examples of suitable compounds are titanium alkoxides such as titanium tetraisopropoxide, acyl trialkyl titanates such as acetyl triisopropyl titanate, and titanium halides such as titanium tetrachloride. The most preferred compound is titanium tetraisopropoxide.

The tertiary amines which are useful in our process are any tertiary amines which significantly enhance the rate of esterification. Examples are triethylamine, tri-n-butylamine, tri-n-hexylamine, tri-2-ethylhexylamine, tridodecylamine, 1,4-dimethylpiperazine, and triethylenediamine. Triethylamine, tri-n-butylamine, tri-n-hexylamine, 1,4-dimethylpiperazine and triethylenediamine are preferred and triethylamine is the most preferred.

The amount of titanium-containing compound can be any amount which significantly enhances the esterification rate. Preferably the amount is that amount which is sufficient to provide 10 to 10,000 weight parts per million titanium, based on the weight of the impure bis(2-hydroxyethyl) ester of 2,6-naphthalenedicarboxylic acid. More preferably the amount is that amound which is sufficient to provide 500 to 600 weight parts per million titanium, based on the weight of the impure bis(2-hydroxyethyl) ester of 2,6-naphthalenedicarboxylic acid.

The amount of tertiary amine can be any amount which significantly enhances the rate of esterification. Preferably the amount of tertiary amine is in the range of about 0.015 to about 0.030 mole, based on the moles of impure bis(2-hydroxyethyl) ester of 2,6-naphthalenedicarboxylic acid.

The second step of crystallizing the ester can be accomplished by any number of means well known in the art. Since the ester is relatively insoluble in cold ethylene glycol, the reaction mixture can be chilled to accomplish crystallization. Alternatively the reaction mixture can be mixed with another fluid, such as isopropanol, to crystallize the ester.

The third step of recovering the crystallized ester can be accomplished by methods well known in the art, such as filtration or centrifugation. Filtration is preferred due to cost considerations.

The ester may be further purified by recrystallization from a suitable organic solvent such as isopropanol or ethanol. Decolorizing carbon and filter aids may be added during the recrystallization operation, if desired.

The following examples are presented to illustrate the invention.

EXAMPLE 1

The following reactants were heated eight hours in a glass liner in an autoclave at 225° C. under autogenous pressure: impure 2,6-naphthalenedicarboxylic acid—10.8 g (0.05 m), ethylene glycol—82 g (1.32 m), 0.3 g triethylamine, and one drop of titanium tetraisopropoxide. As the reaction mixture was cooled to 23° C., the ester crystallized. The ester was recovered on a filter funnel and washed with methanol. The weight of ester was 12.7 g (83.5%). The product was recrystalized from isopropanol to give a material having a melting point of 144° to 146.5° C.

EXAMPLE 2

In a 300-mL, three-necked flask were placed 10.8 g (0.05 m) of 2,6-naphthalenedicarboxylic acid, 82 g (1.32 m) of ethylene glycol, 0.3 g tributylamine, and two drops of titanium tetraisopropoxide. The flask was fitted with a mechanical stirrer and thermometer and attached to a six-inch, vacuum jacketed column packed with glass Raüschig rings and topped with a still head. The flask was surrounded with a metal bath controlled at 210° C. During the course of about 3.5 hours, mostly at an internal temperature of 198° to 200° C., the mixture became clear. The mixture was held at 198° to 200° C. for about 1.5 hours longer and was then cooled and the ester crystallized. The crystallized ester was recovered by filtration. The weight of the ester was 14.75 g (97% of theory). It melted at 143° to 145° C.

EXAMPLE 3

A. In a 300-mL, three-necked flask were placed 10.8 g (0.05 m) of 2,6-naphthalenedicarboxylic acid, 41 g (0.66 m) of ethylene glycol, and 0.3 g tributylamine. The flask was fitted as described in Example 2. The flask was heated at an internal temperature of 200° to 202° C. during a reaction time of 7 hours and 45 minutes. At the end of this period, the reaction still contained solid material. This is indicative of incomplete reaction, i.e., the 2,6-naphthalenedicarboxlic acid is not completely esterified.

B. When the procedure described in Example 3A was repeated with the exception that two drops of titanium tetraisopropoxide was added, the reaction mixture became clear during a heating period of two hours at 197° to 202° C.

C. When the procedure described in Example 3B was repeated with the exception that the tributylamine was not added, the reaction mixture did not become clear until after 4 hours and 35 minutes heating at a reaction temperature of 200° to 202° C.

While the invention has been described in detail with particular reference to preferred embodiments thereof, it will be understood that variations and modifications can be effected within the spirit and scope of the invention.

We claim:

1. A process for preparation of purified, crystalline bis(2-hydroxyethyl) ester of 2,6-naphthalenedicarboxylic acid comprising
(a) preparing the bis(2-hydroxyethyl) ester of 2,6-naphthalenedicarboxylic acid by reacting impure 2,6-naphthalenedicarboxylic acid with at least two moles of ethylene glycol per mole of 2,6-naphthalenedicarboxylic acid in the presence of a catalytic amount of a tertiary amine and a titanium-containing compound,
(b) crystallizing the bis(2-hydroxyethyl) ester of 2,6-naphthalenedicarboxylic acid, and
(c) recovering the purified, crystalized bis(2-hydroxyethyl) ester of 2,6-naphthalenedicarboxylic acid.

2. The process of claim 1 wherein the tertiary amine is triethylamine, tri-n-butylamine, tri-n-hexylamine, 1,4-dimethylpiperazine or triethylenediamine.

3. The process of claim 2 wherein the tertiary amine is triethylamine.

4. The process of claim 1 wherein the titanium-containing compound is a titanium alkoxide or acetyl triisopropyl titanate.

5. The process of claim 4 wherein the titanium-containing compound is titanium tetraisopropoxide.

6. The process of claim 1 wherein the amount of titanium-containing compound is sufficient to provide 10 to 10,000 weight parts per million titanium, based on the weight of the impure bis(2-hydroxyethyl) ester of 2,6-naphthalenedicarboxylic acid.

7. The process of claim 6 wherein the amount of titanium-containing compound is sufficient to provide 500 to 600 weight parts per million titanium, based on the weight of the impure bis(2-hydroxyethyl) ester of 2,6-naphthalenedicarboxylic acid.

8. The process of claim 1 wherein the amount of tertiary amine is in the range of about 0.015 to about 0.030 moles, based on the moles of impure bis(2-hydroxyethyl) ester of 2,6-naphthalenedicarboxylic acid.

* * * * *